(12) United States Patent
Inoue et al.

(10) Patent No.: US 8,197,800 B2
(45) Date of Patent: Jun. 12, 2012

(54) HAIR TREATING AGENT

(75) Inventors: Katsuhisa Inoue, Wakayama (JP); Takeshi Kaharu, Tokyo (JP)

(73) Assignee: Kao Corporation, Tokyo (JP)

( * ) Notice: Subject to any disclaimer, the term of this patent is extended or adjusted under 35 U.S.C. 154(b) by 691 days.

(21) Appl. No.: 11/392,621

(22) Filed: Mar. 30, 2006

(65) Prior Publication Data

US 2006/0233734 A1 Oct. 19, 2006

(30) Foreign Application Priority Data

Apr. 5, 2005 (JP) .................................. 2005-108943

(51) Int. Cl.
*A61K 8/00* (2006.01)
*A61Q 5/12* (2006.01)
(52) U.S. Cl. .................................. 424/70.21; 424/70.12
(58) Field of Classification Search .................. None
See application file for complete search history.

(56) References Cited

U.S. PATENT DOCUMENTS

| | | | | | |
|---|---|---|---|---|---|
| 4,954,335 | A | * | 9/1990 | Janchipraponvej | 424/70.28 |
| 5,456,863 | A | * | 10/1995 | Bergmann | 510/122 |
| 2004/0234489 | A1 | * | 11/2004 | Muller | 424/70.22 |

FOREIGN PATENT DOCUMENTS

| | | |
|---|---|---|
| DE | 195 36 420 A1 | 4/1996 |
| EP | 0 867 168 A2 | 9/1998 |
| EP | 0 885 607 A2 | 12/1998 |
| EP | 0885607 A2 | 12/1998 |
| EP | 1 462 086 A1 | 9/2004 |
| EP | 1 462 087 A2 | 9/2004 |
| EP | 1 493 424 A1 | 1/2005 |
| JP | 6-9346 | 1/1994 |
| JP | 6-128202 | 5/1994 |
| JP | A-06-128202 | 5/1994 |
| JP | A 08-099841 | 4/1996 |
| JP | 9-118606 | 5/1997 |
| JP | A 10-273429 | 10/1998 |
| JP | 2987667 | * 12/1999 |
| JP | A-2002-332219 | 11/2002 |
| JP | A-2004-002261 | 1/2004 |
| WO | WO 99/11226 | * 3/1999 |
| WO | WO-03-084492 A1 | 10/2003 |

OTHER PUBLICATIONS

Machine-generated English language translation of JPB-2987667.*
Machine-generated English language translation of JPB-2987667, 2009.*
Extended European Search Report issued May 13, 2011, in Patent Application No. 10185740.7.
Office Action issued Apr. 22, 2010, in Europe Patent Application No. 06007038.0-2108/1733712.
Office Action issued Oct. 21, 2010 in China, Patent Application No. 200610066381.9 with English Language Translation.
Feb. 1, 2011 Japanese Office Action corresponding to Japanese patent application 2005-108943.

* cited by examiner

*Primary Examiner* — Brian Gulledge
(74) *Attorney, Agent, or Firm* — Oblon, Spivak, McClelland, Maier & Neustadt, L.L.P.

(57) ABSTRACT

The present invention relates to a hair treating agent containing (a) an organic acid represented by the formula (1), an organic acid represented by the formula (2) or their salts and (b) a quaternary ammonium salt, a tertiary amine or a salt thereof:

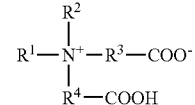

(1)

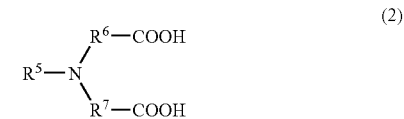

(2)

wherein $R^1$ and $R^2$ independently represent an alkyl or hydroxyalkyl group having 1 to 5 carbon atoms or $-R^8-COOH$, $R^3$, $R^4$ and $R^8$ independently represent an alkylene group having 1 to 5 carbon atoms, $R^5$ represent an alkyl or hydroxyalkyl group having 1 to 5 carbon atoms or $-R^9-COOH$ and $R^6$, $R^7$ and $R^9$ independently represent an alkylene group having 1 to 5 carbon atoms.

17 Claims, No Drawings

HAIR TREATING AGENT

FIELD OF THE INVENTION

The present invention relates to a hair treating agent.

BACKGROUND OF THE INVENTION

It is demanded of hair treating agents such as a shampoo, rinse, conditioner, treatment, hair dyeing agent and moose to impart softness, smoothness and oily feel to the hair, and smoothness and well-combing characteristics to the hair after the hair is dried with the view of protecting the hair and improving a feel to the touch when these agents are used. Based on such a demand, a quaternary ammonium salt or an amine salt is currently formulated. As the counter ions of these salts, for example, halogen ions such as Cl⁻ and Br⁻, or short-chain alkylsulfuric acid ions such as methylsulfuric acid and ethylsulfuric acid (JP-A 6-9346) and organic acid ions such as acetic acid, tartaric acid, lactic acid, malic acid, succinic acid and carboxylic acids or sulfonic acids having a long-chain alkyl group (WO-A99/11226 and JP-A 9-118606) are reported.

SUMMARY OF THE INVENTION

The present invention relates to a hair treating agent containing the following components (a) and (b):

(a): at least one compound selected from an organic acid (hereinafter, referred to as an organic acid (1)) represented by the formula (1), an organic acid (hereinafter, referred to as an organic acid (2)) represented by the formula (2) or their salts;

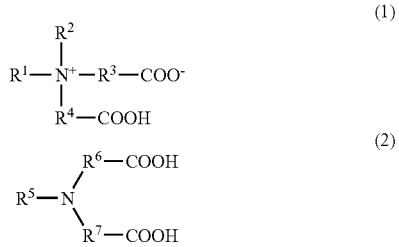

wherein $R^1$ and $R^2$ independently represent a straight-chain or branched alkyl or hydroxyalkyl group having 1 to 5 carbon atoms or —$R^8$—COOH, $R^3$, $R^4$ and $R^8$ independently represent a straight-chain or branched alkylene group having 1 to 5 carbon atoms, $R^5$ represent a straight-chain or branched alkyl or hydroxyalkyl group having 1 to 5 carbon atoms or —$R^9$—COOH and $R^6$, $R^7$ and $R^9$ independently represent a straight-chain or branched alkylene group having 1 to 5 carbon atoms; and (b): at least one compound selected from a quaternary ammonium salt and a tertiary amine or a salt thereof.

DETAILED DESCRIPTION OF THE INVENTION

Any of the hair treating agents in the above prior technologies insufficiently satisfies a good feel in use when or after applied to the hair.

The present invention relates to a hair treating agent that can impart softness, smoothness and an oily feel to the hair during the course of washing and rinsing after it is applied to the hair, and smoothness and well-combing characteristics to the hair after the hair is dried.

It has been found in the present invention that softness, smoothness and an oily feel during the course of washing and rinsing after it is applied to the hair, and smoothness and well-combing characteristics after the hair is dried can be imparted to the hair by using a specified organic acid as the counter ion of a quaternary ammonium salt or a tertiary amine salt.

The hair treating agent of the present invention can impart sufficient softness, smoothness and oily feel during the course of washing and rinsing after it is applied to the hair, and smoothness and well-combing characteristics to the hair after the hair is dried.

[Component (a)]

The component (a) of the present invention is at least one compound selected from the organic acids (1) and (2) or their salts.

In the organic acid (1), $R^1$ and $R^2$ independently represent a straight-chain or branched alkyl or hydroxyalkyl group having 1 to 5 carbon atoms or —$R^8$—COOH. $R^1$ and $R^2$ are independently preferably a straight-chain or branched alkyl or hydroxyalkyl group having 1 to 3 carbon atoms or —$R^8$—COOH and more preferably a methyl group, an ethyl group or a hydroxyalkyl group having 1 to 3 carbon atoms. As the hydroxyalkyl group having 1 to 3 carbon atoms, a hydroxyethyl group, a 2,3-dihydroxypropyl group, a 1-methyl-2-hydroxyethyl group or a 2-hydroxypropyl group is preferable. $R^3$, $R^4$ and $R^8$ independently represent a straight-chain or branched alkylene group having 1 to 5 carbon atoms. $R^3$, $R^4$ and $R^8$ are independently preferably a straight-chain or branched alkylene group having 1 to 3 carbon atoms and more preferably a methylene group.

In the organic acid (2), $R^5$ represent a straight-chain or branched alkyl or hydroxyalkyl group having 1 to 5 carbon atoms or —$R^9$—COOH. $R^5$ is preferably a straight-chain or branched alkyl or hydroxyalkyl group having 1 to 3 carbon atoms or —$R^9$—COOH and more preferably a methyl group, an ethyl group or a hydroxyalkyl group having 1 to 3 carbon atoms. As the hydroxyalkyl group having 1 to 3 carbon atoms, a hydroxyethyl group, a 2,3-dihydroxypropyl group, a 1-methyl-2-hydroxyethyl group or a 2-hydroxypropyl group is preferable. $R^6$, $R^7$ and $R^9$ independently represent a straight-chain or branched alkylene group having 1 to 5 carbon atoms. $R^6$, $R^7$ and $R^9$ are independently preferably a straight-chain or branched alkylene group having 1 to 3 carbon atoms and more preferably a methylene group.

No particular limitation is imposed on a method of synthesizing the organic acids (1) and (2). Examples of the method of synthesizing the organic acids (1) and (2) include a method in which a carboxylic acid halide or a salt thereof is reacted with a corresponding amine and the by-produced inorganic salt is removed according to the need, a method in which a lower alkyl ester of a carboxylic acid halide is reacted with a corresponding amine and the reaction product is then hydrolyzed, a method in which an alkyl halogen or epoxides such as glycidol or ethylene oxide is reacted with an aminocarboxylic acid or a salt thereof and the by-produced inorganic salt is removed according to the need, a method in which a STRECKER's reaction of a corresponding amine is carried out, then the reaction product is hydrolyzed and the by-produced inorganic salt is removed according to the need as the method of obtaining the organic acid (2), and a method in which an alkyl halogen, oxides such as ethylene oxide, carboxylic acid halide or a salt thereof or lower alkyl ester is further reacted with the organic acid (2) and then, according to the need, the by-produced inorganic salt is removed and the ester is hydrolyzed as the method of obtaining the organic acid (1)

Examples of the salt of the organic acid (1) or (2) include salts of alkali metals such as Na and K and substituted or unsubstituted ammonium salts.

[Component (b)]

The component (b) of the present invention is at least one compound selected from a quaternary ammonium salt and tertiary amine or a salt thereof.

As the component (b), any compound maybe used without any particular limitation insofar as it reacts with the organic acid (1) or (2) to form a salt to be a cationic surfactant. The component (b) is preferably a quaternary ammonium salt represented by the formula (3) or a tertiary amine represented by the formula (4) or a salt thereof. More preferably, the component (b) has at least one compound containing a tertiary amine represented by the formula (4) or a salt thereof and even more preferably has at least one compound containing a tertiary amine represented by the formula (4).

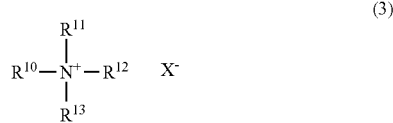
(3)

In the formula, $R^{10}$ represents a straight-chain or branched alkyl or alkenyl group having 8 to 30 carbon atoms wherein the alkyl or alkenyl group may be divided by an ester group, amide group or ether group, $R^{11}$ represents a straight-chain or branched alkyl or alkenyl group having 8 to 30 carbon atoms wherein the alkyl or alkenyl group may be divided by an ester group, amide group or ether group, or a straight-chain or branched alkyl or hydroxyalkyl group having 1 to 3 carbon atoms, $R^{12}$ and $R^{13}$ independently represent a straight-chain or branched alkyl or hydroxyalkyl group having 1 to 3 carbon atoms and X-represents an anion.

(4)

In the formula, $R^{14}$ represents a straight-chain or branched alkyl group or alkenyl group having 8 to 30 carbon atoms wherein the alkyl or alkenyl group may be divided by an ester group, amide group or ether group, $R^{15}$ represents a straight-chain or branched alkyl or alkenyl group having 8 to 30 carbon atoms wherein the alkyl or alkenyl group may be divided by an ester group, amide group or ether group, or a straight-chain or branched alkyl group or hydroxyalkyl group having 1 to 3 carbon atoms and $R^{16}$ represents a straight-chain or branched alkyl or hydroxyalkyl group having 1 to 3 carbon atoms.

In the formula (3), $R^{10}$ is preferably a straight-chain or branched alkyl group having 10 to 28 carbon atoms wherein the alkyl group may be divided by an ester group, amide group or ether group and even more preferably a straight-chain or branched alkyl group having 14 to 24 carbon atoms wherein the alkyl group maybe divided by an ester group, amide group or ether group. $R^{11}$ is preferably a straight-chain or branched alkyl group having 14 to 24 carbon atoms wherein the alkyl group maybe divided by an ester group, amide group or ether group, or a straight-chain or branched alkyl or hydroxyalkyl group having 1 to 3 carbon atoms, more preferably a straight-chain or branched alkyl group having 1 to 3 carbon atoms and even more preferably a methyl group or an ethyl group. $R^{12}$ and $R^{13}$ are independently preferably a methyl group or an ethyl group. Examples of the anion represented by X- include a halogen ions such as Cl- and Br-, short-chain alkylsulfuric acid ions such as a methylsulfuric acid ion and ethylsulfuric acid ion and ions of organic acids such as acetic acid, tartaric acid, lactic acid, malic acid and succinic acid. Among these ions, halogen ions and short-chain alkylsulfuric acid ions are preferable.

In the formula (4), $R^{14}$ is preferably a straight-chain or branched alkyl group having 10 to 28 carbon atoms wherein the alkyl group maybe divided by an ester group, amide group or ether group and more preferably a straight-chain or branched alkyl group having 14 to 24 carbon atoms wherein the alkyl group may be divided by an ester group, amide group or ether group. $R^{15}$ is preferably a straight-chain or branched alkyl or alkenyl group having 14 to 24 carbon atoms wherein the alkyl or alkenyl group may be divided by an ester group, amide group or ether group, or a straight-chain or branched alkyl or hydroxyalkyl group having 1 to 3 carbon atoms and more preferably a straight-chain or branched alkyl or hydroxyalkyl group having 1 to 3 carbon atoms. $R^{16}$ is preferably a methyl group, an ethyl group or a hydroxyethyl group and more preferably a methyl group or an ethyl group.

Examples of the salts of tertiary amines represented by the formula (4) are salts of inorganic acids such as hydrochloric acid, sulfuric acid and phosphoric acid and salts of organic acids such as acetic acid, tartaric acid, lactic acid, malic acid and succinic acid.

[Hair Treating Agent]

The content of the component (a) in the hair treating agent of the present invention is preferably 0.1 to 20 moles, more preferably 0.3 to 10 moles, even more preferably 0.5 to 5 moles, to 1 mole of the component (b) from the viewpoint of giving the hair a good feel to the touch and suppressing layer separation and solidification to thereby obtaining the high stability of the product. Also, the content of the component (b) in the hair treating agent is preferably 0.1 to 20% by weight, more preferably 0.2 to 15% by weight and even more preferably 0.5 to 10% by weight. Also, the pH of the hair treating agent is preferably 2 to 12, more preferably 3 to 11 from the viewpoint of imparting a conditioning effect and even more preferably 3 to 6 from the viewpoint of imparting the hair a good feel to the touch and the stability of a product.

The hair treating agent preferably further contains an oily component. Examples of the oily component of the present invention include a higher alcohol, ester oil, silicone and hydrocarbons. Among these compounds, a higher alcohol, oil agent such as an ester oil and/or silicone are preferable and a higher alcohol and/or silicone are more preferable.

Examples of the higher alcohols used in the present invention include higher alcohols having a straight-chain or branched alkyl or alkenyl group having 10 to 30 carbon atoms. Among these alcohols, higher alcohols having a straight-chain or branched alkyl or alkenyl group having 12 to 26 carbon atoms are preferable and cetanol, cetyl alcohol, stearyl alcohol, arachil alcohol, behenyl alcohol, caranaubil alcohol and ceryl alcohol are more preferable.

Examples of the ester oil include esters of fatty acids having 8 to 40 carbon atoms and straight-chain or branched alcohols having 1 to 4 carbon atoms. The ester is preferably esters of fatty acids having 10 to 24 carbon atoms and straight-chain or branched alcohols having 1 to 3 carbon atoms and more preferably esters of fatty acids having 12 to 22 carbon atoms and propyl alcohol or isopropyl alcohol.

Examples of the silicone to be used in the present invention include dimethylpolysiloxane, methylphenylpolysiloxane, amino-modified silicone, fatty acid-modified polysiloxane, alcohol-modified silicone, aliphatic alcohol-modified polysiloxane, polyether-modified silicone, epoxy-modified silicone, fluorine-modified silicone, cyclic silicone and alkyl-modified silicone.

The content of the oily component in the hair treating agent of the present invention is preferably 0.1 to 30% by weight, more preferably 0.5 to 25% by weight and even more preferably 1 to 20% by weight from the viewpoint of the good feel of hair to the touch and emulsion/dispersion stability of the oily component.

In the hair treating agent of the present invention, for example, other surfactants such as anionic surfactants, nonionic surfactants and amphoteric surfactants, lanolin derivatives, higher fatty acid esters, higher fatty acids, fatty acids, glycerin, amino acid, humectant, cationic polymer, polysaccharides, polypeptide, pearling agent, solvent, liquid crystal forming agent, inorganic acid, organic acid, dyes, perfumes, ultraviolet absorber, antioxidant, propellant, chelating agent, pH regulator, antiseptic and antidandruff agent may be formulated to the extent that the object of the present invention is not impaired.

The hair treating agent of the present invention may be made into a desired preparation form such as an aqueous solution, ethanol solution, emulsion, suspension, gel, liquid crystal and aerosol.

The hair treating agent of the present invention may be used for a hair rinse, hair conditioner, hair treatment, hair pack, hair cream, conditioning moose, hair moose, hair spray, leave-on treatment, shampoo, hair lotion shampoo, hair dyeing agent and hair breaching agent.

EXAMPLES

The following examples are examples of the present invention. These examples are described as to examples of the present invention and are not intended to be limiting of the present invention.

In the following examples, "%" means % by weight, unless otherwise specified.

Synthetic Example 1

A four-neck flask equipped with a stirrer, a temperature gage and a cooling tube was charged with 180.3 g of an aqueous 50% dimethylamine solution (manufactured by Wako Pure Chemical Industries, Ltd.) and 400 g of ion exchange water. 475.4 g of sodium chloroacetate. (manufactured by Wako Pure Chemical Industries, Ltd.) was added dropwise to the mixture at 20 to 30° C. and the resulting mixture was reacted at 20 to 30° C. for one hour. Next, 166.7 g of an aqueous 48% sodium hydroxide solution was added to the reaction mixture for 0.5 hours while keeping the mixture at 20 to 30° C. and the resulting mixture was further reacted at 35 to 40° C. for 3 hours. After the reaction was completed, 202.6 g of an aqueous 36% hydrochloric solution was added dropwise to the reaction mixture, which was then mixed at 10 to 20° C. for 2 hours with stirring. Then, the precipitated crystals were collected by filtration, then washed with 440 g of water and dried to obtain 226.7 g of the organic acid A shown in Table 1.

Synthetic Example 2

A four-neck flask equipped with a stirrer, a temperature gage and a cooling tube was charged with 133.1 g of iminodiacetic acid (Wako pure Chemical Industries, Ltd.), 120 g of ion exchange water and 166.7 g of an 48% aqueous sodium hydroxide solution. 103.7 g of glycidol (obtained by refining a product of Wako pure Chemical Industries, Ltd. by distillation) was added to the mixture over one hour while the mixture was kept at 20 to 30° C. and the resulting mixture was reacted at 30 to 40° C. for 5 hours. After the reaction was finished, the mixture was subjected to crystallization from ethanol, and the crystals were collected by filtration and dried to obtain 238 g of a white powder. Next, a beaker was charged with 226.0 g of the white powder and 452 g of ion exchange water and 182.5 g of an aqueous 36% hydrochloric solution was added to the mixture, which was then desalted by electrodialysis and then freeze-dried to obtain 168.1 g of the organic acid B shown in Table 1.

The components (a) used in the following examples are listed in Table 1. The components (b) used in the following examples are listed in Table 2.

TABLE 1

| Organic acid A | $\begin{array}{c} CH_3 \\ \phantom{CH_3}\diagdown \\ \phantom{CH_3}\phantom{\diagdown}N^+ \\ CH_3\diagup\phantom{N^+}\diagdown \end{array} \begin{array}{c} CH_2-COO^- \\ \\ CH_2-COOH \end{array}$ |
|---|---|
| | Purity 99.0% (Others: NaCl, water and the like) |
| Organic acid B | $HO-CH_2-\underset{\underset{OH}{\mid}}{CH}-CH_2-N\diagup\overset{CH_2-COOH}{\diagdown CH_2-COOH}$ |
| | Purity 96.1% (Others: NaCl, iminodiacetic acid, water and the like) |
| Organic acid C*[1] | $HO-CH_2-CH_2-N\diagup\overset{CH_2-COOH}{\diagdown CH_2-COOH}$ |
| | Purity 99% |
| Organic acid D*[2] | $CH_3-N\diagup\overset{CH_2-COOH}{\diagdown CH_2-COOH}$ |
| | Purity >98% |

*[1]N-(2-hydroxyethyl) iminodiacetic acid manufactured by Tokyo Kasei Kogyo Co., Ltd.
*[2]Methyliminodiacetic acid manufactured by Sigma Aldrich Japan Corp.

*1: N-(2-hydroxyethyl)iminodiacetic acid manufactured by Tokyo Kasei Kogyo Co., Ltd.
*2: Methyliminodiacetic acid manufactured by Sigma Aldrich Japan Corp.

TABLE 2

| (b-1) | $C_{17}H_{35}-\overset{O}{\underset{\|}{C}}-\overset{H}{\underset{\|}{N}}-C_3H_6-N\diagup\overset{CH_3}{\diagdown CH_3}$ |
|---|---|
| | NIKKOL amidoaminw MPS manufactured by Nikko Chemicals Co., Ltd. |
| (b-2) | $R-\overset{O}{\underset{\|}{C}}-\overset{H}{\underset{\|}{N}}-C_3H_6-N\diagup\overset{CH_3}{\diagdown CH_3}$ |
| | R: $C_{17}H_{35}/C_{19}H_{39}/C_{21}H_{43}/C_{23}H_{47}$ = 1/7/89/2% Purity 99.1% (Others: fatty acid, water and the like) |

TABLE 2-continued (b-3)

$$C_{17}H_{35}-O-C_3H_6-N\begin{matrix}CH_3\\ \\CH_3\end{matrix}$$

Purity 93% (Others: stearyl alcohol and the like)
Farmine DM-E80 manufactured by Kao Corporation (b-4)

$$C_{18}H_{37}-\underset{\underset{CH_3}{|}}{\overset{\overset{CH_3}{|}}{N^+}}-CH_3 \quad Cl^-$$

Purity >97%
Trimethylstearylammonium chloride manufactured by Tokyo Chemical Industry Co., Ltd.

Examples 1 to 4 and Comparative Examples 1 to 3

Each of the organic acids A to D or, as the comparative acids, lactic acid, L-glutamic acid or hydrochloric acid was used as the component (a) and (b-1) was used as the component (b) to prepare hair rinsing agents having the compositions shown in Table 3 by the conventional method. With regard to these hair rinsing agents, the abilities of each agent when it was applied and rinsed and after it was dried were evaluated. The results are shown in Table 3.

<Method of Evaluation>

20 g of the hair (length: 20 cm and average diameter: 60 μm) of a Japanese woman having no experience of chemical treatment such as a cold perm was tied up in a bundle, which was then washed with 5 g of a shampoo. The composition of the shampoo had 15% of sodium polyoxyethylene alkyl (12 carbon atoms) ether sulfate (ethylene oxide average addition mol number: 2.5) and 3% of diethanolamide which was balanced with water.

After that, 2.0g of a hair rinsing agent was uniformly applied to the hair and the hair was rinsed with a running water at 40° C. for 30 seconds.

The softness and smoothness of the hair when the hair rinsing agent was applied and the hair was rinsed, an oily feel when the hair rinsing agent was applied, a smooth feel retentivity when the hair was rinsed and a smooth feel and a combing feel after the hair was dried were functionally evaluated by five expert panelists according to the following standard.

⊙: Four or more panelists answered that the hair rinsing agent had an effect.

○: Three panelists answered that the hair rinsing agent had an effect.

Δ: Two panelists answered that the hair rinsing agent had an effect.

×: One or less panelist answered that the hair rinsing agent had an effect.

TABLE 3

| | | | Example | | | | Comparative example | | |
|---|---|---|---|---|---|---|---|---|---|
| | | | 1 | 2 | 3 | 4 | 1 | 2 | 3 |
| Percentage composition of the hair rinsing agent (%) | Organic acid (molar ratio to the component (b)) | | A 1.0 | B 1.0 | C 1.0 | D 1.0 | — | — | — |
| | Comparative acid (molar ratio to the component (b)) | | — | — | — | — | Lactic acid 1.0 | L-glutamic acid 1.0 | Hydrochloric acid 1.0 |
| | Component (b) | | (b-1) 1.5 | (b-1) 1.5 | (b-1) 1.5 | (b-1) 1.5 | (b-1) 1.5 | (b-1) 1.5 | (b-1) 1.5 |
| | Stearyl alcohol | | 4.5 | 4.5 | 4.5 | 4.5 | 4.5 | 4.5 | 4.5 |
| | Dimethylpolysiloxane*¹ | | 2 | 2 | 2 | 2 | 2 | 2 | 2 |
| | Citric acid (pH regulator) | | Proper amount | Proper amount | Proper amount | Proper amount | Proper amount | Proper amount | Proper amount |
| | Purified water | | Balance | Balance | Balance | Balance | Balance | Balance | Balance |
| | pH | | 4.0 | 4.0 | 4.0 | 4.0 | 4.0 | 4.3 | 4.0 |
| Results of evaluation | When the rinsing agent is apolied | Softness | ⊙ | ⊙ | ⊙ | ⊙ | ○ | Δ | Δ |
| | | Smoothness | ○ | ○ | ○ | ○ | Δ | ○ | × |
| | | Oil feel | ○ | ○ | ○ | ○ | Δ | Δ | Δ |
| | When the hair is rinsed | Softness | ⊙ | ○ | ⊙ | ○ | ○ | Δ | Δ |
| | | Smoothness | ○ | ○ | ○ | ○ | Δ | ○ | × |
| | | retentivity of smooth feel | ○ | ○ | ⊙ | ○ | Δ | Δ | × |
| | After the hair is dried | Smooth feel | ⊙ | ○ | ○ | ○ | Δ | Δ | Δ |
| | | Combing feel | ○ | ○ | ⊙ | ○ | Δ | Δ | Δ |

*¹BY25-320 manufactured by Dow Corning Toray Silicone Co., Ltd.

Examples 5 to 8

The organic acids and the component (b) shown in Table 4 were used to produce hair rinsing agents having the compositions shown in Table 4 by the conventional method. The performances of these hair rinsing agents when these agents were applied to the hair, when the hair was rinsed and after the hair was dried were evaluated in the same manner as in Example 1. The results are shown in Table 4.

TABLE 4

|  |  |  | Example | | | |
|---|---|---|---|---|---|---|
|  |  |  | 5 | 6 | 7 | 8 |
| Percentage composition of the hair rinsing agent (%) | Acid (molar ratio to the component (b)) | Organic acidA | | | 1.0 | |
| | | Organic acidC | 1.1 | 1.1 | | 0.8 |
| | | Lactic acid | | | 0.5 | 0.8 |
| | Component (b) | (b-1) | | | 0.8 | |
| | | (b-2) | 1.5 | | 0.8 | 1.0 |
| | | (b-3) | | 1.5 | | |
| | | (b-4) | | | | 0.6 |
| | Cetyl alcohol | | 1 | | 2 | 1 |
| | Stearyl alcohol | | 3 | 4 | 5 | 1 |
| | Behenyl alcohol | | 1 | 2 | | 3 |
| | Liquid paraffin | | 2 | 2 | 1 | 1 |
| | Dimethylpolysiloxane*[1] | | 1 | 2 | 2 | 3 |
| | Phosphoric acid (pH regulator) | | Proper amount | Proper amount | Proper amount | Proper amount |
| | Purified water | | Balance | Balance | Balance | Balance |
| | pH | | 3.8 | 3.8 | 3.6 | 3.6 |
| Results of evaluation | When the rinsing agent is applied | Softness | ◎ | ◎ | ◎ | ◎ |
| | | Smoothness | ○ | ○ | ◎ | ○ |
| | | Oily feel | ◎ | ○ | ○ | ○ |
| | When the hair is rinsed | Softness | ○ | ○ | ◎ | ◎ |
| | | Smoothness | ◎ | ◎ | ○ | ○ |
| | | retentivity of smooth feel | ○ | ◎ | ◎ | ○ |
| | After the hair is dried | Smooth feel | ◎ | ◎ | ○ | ○ |
| | | Combing feel | ◎ | ○ | ◎ | ◎ |

*[1]BY25-320 manufactured by Dow Corning Toray Silicone Co., Ltd.

Example 9

A hair conditioner having the following composition was produced. This hair conditioner was good in hair softness, smoothness and oil feel when it was applied to hair and rinsed and then smoothness and combing after the hair was dried.

<Composition>

| | |
|---|---|
| Organic acid A | 0.6% |
| (b-2) | 1.6% |
| Stearyl alcohol*[1] | 4.0% |
| Glycerin | 1.0% |
| Benzyloxyethanol | 0.3% |
| Silicone*[2] | 2.0% |
| Amino-modified silicone-polyoxyalkylene block Copolymer*[3] | 0.5% |
| Dipentaerythritol fatty acid ester*[4] | 0.2% |
| Hydroxyethyl cellulose*[5] | 0.2% |
| Highly polymerized polyethylene glycol*[6] | 0.05% |
| Tocopherol acetate | 0.1% |
| Perfume, methyl parabene | Proper amount |
| Purified water | Balance |

(pH 4.5)
*[1]Kalcol 8098 manufactured by Kao Corporation
*[2]BY00-003 manufactured by Dow Corning Toray Silicone Co., Ltd.
*[3]FZ-3789, manufactured by Nihonunica Corporation
*[4]Cosmol 168AR manufactured by Nisshin Seiyu Corp.
*[5]SE-850 manufactured by Daicel Chemical Industries, Ltd.
*[6]Polyox WSRN-60K manufactured by Union Carbide Corporation

Example 10

A hair treatment having the following composition was produced. This hair treatment was good in hair softness, smoothness and oil feel when it was applied to hair and rinsed and then smoothness and combing after the hair was dried.

<Composition>

| | |
|---|---|
| Organic acid C | 1.1% |
| (b-3) | 2.5% |
| Stearyl alcohol | 4.5% |
| Behenyl alcohol*[1] | 1.5% |
| Isononyl isononanate*[2] | 0.5% |
| Silicone*[3] | 1.0% |
| Amino-modified silicone*[4] | 0.5% |
| Malic acid | 0.1% |
| Dipropylene glycol | 3.0% |
| Benzyl alcohol | 0.3% |
| Alginine | 0.2% |
| Pantotenyl ethyl ether | 0.1% |
| Perfume, methyl parabene | Proper amount |
| Purified water | Balance |

(pH 4.0)
*[1]Kalcol 22080 manufactured by Kao Corporation
*[2]Salakos 99 manufactured by Nisshin Seiyu Corp.
*[3]SH200C-5000 cs manufactured by Dow Corning Toray Silicone Co., Ltd.
*[4]SM8704C manufactured by Dow Corning Toray Silicone Co., Ltd.

The invention claimed is:

1. A hair treating agent comprising the following components (a) and (b):

(a): at least one compound selected from the group consisting of an organic acid represented by the formula (1) and an organic acid represented by the formula (2) or a salt thereof:

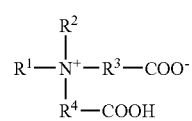

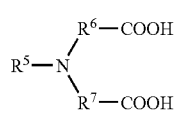

(2)

wherein $R^1$ and $R^2$ independently represent methyl, ethyl or hydroxyalkyl group having 1 to 3 carbon atoms, $R^3$ and $R^4$ independently represent a straight-chain or branched alkylene group having 1 to 3 carbon atoms, $R^5$ represent methyl, ethyl or hydroxyalkyl group having 1 to 3 carbon atoms and $R^6$ and $R^7$ independently represent a straight-chain or branched alkylene group having 1 to 3 carbon atoms; and (b): 0.1 to 10 wt. % of at least one compound selected from the group consisting of a tertiary amine represented by the formula (4) or a salt thereof:

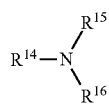

(4)

wherein $R^{14}$ represents a straight-chain or branched alkyl group or alkenyl group having 8 to 30 carbon atoms wherein the alkyl or alkenyl group may be divided by an ester group, an amide group or an ether group, $R^{15}$ represents a straight-chain or branched alkyl group or hydoxyalkyl group having 1 to 3 carbon atoms, and $R^{16}$ represents a straight-chain or branched alkyl or hydroxyalkyl group having 1 to 3 carbon atoms wherein components (a) and (b) are present in an (a)/(b) molar ratio of 0.5 to 5.

2. The hair treating agent according to claim 1, wherein, in the formula (1) or (2), $R^3$ and $R^4$ are independently a methylene group, $R^5$ is methyl, ethyl or hydroxyalkyl group having 1 to 3 carbon atoms and $R^6$ and $R^7$ are independently a methylene group.

3. The hair treating agent according to claim 1 or 2, the agent further comprising an oily component.

4. The hair treating agent according to claim 1, wherein said salt of formula (1) or (2) is a salt of at least one selected from the group consisting of alkali metals, substituted ammonium and unsubstituted ammonium.

5. The hair treating agent according to claim 1 wherein said salt of a tertiary amine is a salt of at least one acid selected from the group consisting of hydrochloric acid, sulfuric acid and phosphoric acid, acetic acid, tartaric acid, lactic acid, malic acid and succinic acid.

6. The hair treating agent according to claim 1, having a pH of from 3 to 6.

7. The hair treating agent according to claim 1, wherein the content of the component (b) is 0.5 to 10% by weight based on the total amount of the hair treating agent.

8. The hair treating agent according to claim 3, wherein said oily component is at least one selected from the group consisting of a higher alcohol, an ester oil, a silicone and a hydrocarbon.

9. The hair treating agent according to claim 3 wherein said oily component is a higher alcohol selected from the group consisting of cetanol, cetyl alcohol, stearyl alcohol, arachil alcohol, behenyl alcohol, caranaubil alcohol and ceryl alcohol and mixture thereof.

10. The hair treating agent according to claim 3, wherein said oily component is a ester oil of an ester of a $C_{12-22}$ fatty acid and propyl alcohol or isopropyl alcohol.

11. The hair treating agent according to claim 3, wherein said oily component is a silicone selected from the group consisting of dimethylpolysiloxane, methylphenylpolysiloxane, amino-modified silicone, fatty acid-modified polysiloxane, alcohol-modified silicone, aliphatic alcohol-modified polysiloxane, polyether-modified silicone, epoxy-modified silicone, fluorine-modified silicone, cyclic silicone, alkyl-modified silicone and a mixture thereof.

12. The hair treating agent according to claim 3, wherein a content of said oily component is 1 to 20% by weight.

13. The hair treating agent according to claim 1, wherein said organic acid is represented by the formula (2) or a salt thereof.

14. The hair treating agent according to claim 1, wherein said organic acid is represented by the formula (1) or a salt thereof.

15. The hair treating agent according to claim 13 wherein said organic acid represented by formula (2) is (2-hydroxyethyl) iminodiacetic acid.

16. The hair treating agent according to claim 1, wherein the content of the component (b) is 0.1 to 2.5% by weight based on the total amount of the hair treating agent.

17. The hair treating agent according to claim 1, wherein $R^{14}$ represents a straight-chain or branched alkyl group or alkenyl group having 8 to 30 carbon atoms wherein said alkyl or alkenyl group is divided by an ester group or an ether group.

* * * * *